(12) United States Patent
Lee et al.

(10) Patent No.: US 10,206,574 B2
(45) Date of Patent: Feb. 19, 2019

(54) APPARATUS AND METHOD FOR ELECTRICAL PROPERTIES TOMOGRAPHY USING MAGNETIC RESONANCE

(71) Applicant: UNIVERSITY-INDUSTRY COOPERATION GROUP OF KYUNG HEE UNIVERSITY, Yongin-si, Gyeonggi-do (KR)

(72) Inventors: Soo Yeol Lee, Yongin-si (KR); Eric Michel, Yongin-si (KR)

(73) Assignees: UNIVERSITY-INDUSTRY COOPERATION GROUP OF KYUNG HEE UNIVERSITY, Yongin-si (KR); SAMSUNG ELECTRONICS CO., LTD., Suwon-si (KR)

( * ) Notice: Subject to any disclaimer, the term of this patent is extended or adjusted under 35 U.S.C. 154(b) by 415 days.

(21) Appl. No.: 15/186,759

(22) Filed: Jun. 20, 2016

(65) Prior Publication Data
US 2016/0367141 A1  Dec. 22, 2016

(30) Foreign Application Priority Data
Jun. 18, 2015 (KR) ........................ 10-2015-0086852

(51) Int. Cl.
*A61B 5/00* (2006.01)
*G01R 33/44* (2006.01)
(Continued)

(52) U.S. Cl.
CPC ............ *A61B 5/0042* (2013.01); *A61B 5/055* (2013.01); *A61B 5/4875* (2013.01); *G01R 33/54* (2013.01);
(Continued)

(58) Field of Classification Search
CPC ..... G01R 33/20-33/586; A61B 5/0042; A61B 5/055; A61B 5/4875
See application file for complete search history.

(56) References Cited

U.S. PATENT DOCUMENTS 6,397,095 B1  5/2002  Eyuboglu et al.
8,064,674 B2  11/2011  Fenchel et al.
(Continued)

FOREIGN PATENT DOCUMENTS

EP  0 851 236 A1  7/1998
JP  2002-209867 A  7/2002
(Continued)

OTHER PUBLICATIONS

Korean Office Action for corresponding Application No. 10-2015-0086852 dated May 11, 2016.

*Primary Examiner* — Tung X Nguyen
*Assistant Examiner* — David Frederiksen
(74) *Attorney, Agent, or Firm* — Sughrue Mion, PLLC (57) ABSTRACT

Disclosed are an apparatus and method for imaging electrical properties of brain tissues including conductivity and permittivity using magnetic resonance imaging (MRI) signals. Electrical properties images for conductivity and permittivity of brain tissues may be obtained with high spatial resolution and high accuracy, without using a derivative which significantly amplifies noise in an MRI image, by calculating water content based on a ratio of MRI signals, calculating electrical properties from the calculated water content, and acquiring an electrical properties image for the calculated electrical properties.

9 Claims, 8 Drawing Sheets

(51) Int. Cl.
  *A61B 5/055*  (2006.01)
  *G01R 33/48*  (2006.01)
  *G01R 33/54*  (2006.01)
  *G01R 33/50*  (2006.01)

(52) U.S. Cl.
  CPC .... *A61B 2576/026* (2013.01); *G01R 33/4828* (2013.01); *G01R 33/50* (2013.01)

(56) References Cited

U.S. PATENT DOCUMENTS

| | | | |
|---|---|---|---|
| 2010/0036453 | A1* | 2/2010 | Hulvershorn .......... A61B 5/055 607/45 |
| 2012/0095700 | A1* | 4/2012 | Novikov ................ B01D 65/10 702/33 |
| 2013/0030500 | A1* | 1/2013 | Toader .................... A61N 1/00 607/45 |
| 2015/0125054 | A1* | 5/2015 | McCollough ......... G06T 11/005 382/131 |

FOREIGN PATENT DOCUMENTS

| | | |
|---|---|---|
| KR | 10-1310706 B1 | 4/2012 |
| KR | 10-2013-0099612 A | 9/2013 |
| KR | 10-2014-0071850 A | 6/2014 |

\* cited by examiner

APPARATUS AND METHOD FOR ELECTRICAL PROPERTIES TOMOGRAPHY USING MAGNETIC RESONANCE

CROSS-REFERENCE TO RELATED APPLICATION

This application claims the priority benefit of Korean Patent Application No. 10-2015-0086852, filed on Jun. 18, 2015 in the Korean Intellectual Property Office, the disclosure of which is incorporated herein by reference.

BACKGROUND OF THE INVENTION

Field of the Invention

The present invention relates to an apparatus and method for electrical properties tomography and, more particularly, to an apparatus and method for imaging electrical properties of brain tissues including conductivity and permittivity using magnetic resonance imaging (MRI) signals.

Description of the Related Art

Techniques for measuring electrical properties of human tissues are broadly divided into Electrical Impedance Tomography (EIT) and Magnetic Resonance Imaging (MRI).

In EIT, a plurality of electrodes is attached to a human body, and electric potential produced when an alternating current is applied to the human body is measured. Then, an image of conductivity distribution in the human body is obtained from the measured electric potential information using an inverse problem solver.

However, for EIT, the resolution of images is very low, and multiple electrodes need to be attached to the epidermis of the human body. For this reason, EIT is not widely used clinically.

With MRI, both the conductivity image and permittivity image of the human body may be obtained. To obtain an MRI image, a radiofrequency magnetic field pulse having the operation frequency of MRI as the center frequency needs to be applied to the human body. The radiofrequency magnetic field pulse changes the hydrogen nucleus to a higher energy level, and the hydrogen atom in a high energy level may trigger a radiofrequency electric potential signal in the radiofrequency coil installed around the human body. The electric potential signal induced in the radiofrequency coil is typically referred to as an MRI signal. An MRI image is obtained from this image signal.

However, since the radiofrequency magnetic field pulse has characteristics of an electromagnetic wave, the wavelength of the electromagnetic wave is greatly shortened within the human body which contains water molecules having high permittivity, and it is difficult to obtain MRI images of a good quality.

Accordingly, the conventional technology for measuring electrical properties of human tissues acquires an image of distribution of $B_1$ through $B_1$ mapping, which is a technique for imaging the magnitude and phase distribution of a radiofrequency magnetic field formed in the human body with MRI, and then uses Magnetic Resonance-Electrical Properties Tomography (MR-EPT) to obtain a conductivity image and a permittivity image from the image of distribution of $B_1$.

With conventional MR-EPT, conductivity and relative permittivity may be calculated from the distribution image of $B_1$ for a region in which uniform conductivity and permittivity are provided, through an inverse problem solver using Equations 1 and 2 given below.

$$\sigma = \frac{1}{\mu\omega} \text{Im}\left\{\frac{\nabla^2 B_1}{B_1}\right\} \quad \text{Equation 1}$$

Herein, σ denotes conductivity, μ denotes the permeability of a radiofrequency magnetic field, and ω denotes an operation frequency of MRI.

$$\varepsilon_r = -\frac{1}{\mu\varepsilon_0\omega^2} \text{Re}\left\{\frac{\nabla^2 B_1}{B_1}\right\} \quad \text{Equation 2}$$

Herein, $\varepsilon_0$ is the free space permittivity and $\varepsilon_r$ denotes relative permittivity.

However, with the MR-EPT technique, Equation 1 for acquiring conductivity and Equation 2 for acquiring permittivity cannot be established in a region in which conductivity and permittivity are not uniform, namely a boundary region where different tissues are adjacent to each other, and thus images of electrical properties obtained from Equation 1 and Equation 2 may have a significant error.

Further, Equations 1 and 2 employ Laplacian ($\nabla^2$), which is a second order derivative, to obtain conductivity and permittivity, but the Laplacian operation tends to significantly amplify noise in performing image measurement. Accordingly, if a $B_1$ distribution image contains noise or has a measurement error, the conductivity image and permittivity image obtained through Equations 1 and 2 may have a significant error.

Moreover, the $B_1$ distribution image contains lots of noise compared to a hydrogen density image, which is a typical MRI image. Accordingly, the conductivity image and permittivity image acquired from the $B_1$ distribution image are typically severely damaged by noise, and thus MR-EPT cannot be used for clinical diagnosis.

Alternatively, in a technology to acquire images of electrical properties of tissue without using the conventional differential calculation, the water content of tissue is acquired using the density of hydrogen atoms, spin-lattice relaxation time $T_1$ and spin-spin relaxation time $T_2$, which are typical physical quantities presented by MRI imaging of the tissue, and a conductivity image and permittivity image are acquired from the acquired water content.

The conventional technology has yielded the Equation 3 below based on the relation between the spin-lattice relaxation time and the water content, which are in close connection with diffusivity of water molecules in a tissue.

$$W = \frac{1}{A + B/T_1} \quad \text{Equation 3}$$

Herein, A and B are constants, which may vary with strength of a main magnetic field of MRI.

$$I_r = \frac{I_s}{I_l} = \kappa \frac{1 - 2e^{-(TR_s - TE/2)/T_1} + e^{-TR_s/T_1}}{1 - 2e^{-(TR_l - TE/2)/T_1} + e^{-TR_l/T_1}} \quad \text{Equation 4}$$

Herein, $I_r$ denotes a ratio for MRI signals, $I_s$ denotes an MRI image signal according to a short repetition time, $I_l$ denotes an MRI image signal according to a long repetition time, $TR_s$ denotes a short repetition time, $TR_l$ denotes a long repetition time, and κ denotes a correction constant.

In the conventional technology, Equation 4 below is produced using MRI image signals acquired from two different repetition times TR, which are imaging variables most widely used in MRI, and an echo time TE, and water content in the tissue is acquired using Equations 3 and 4 as simultaneous equations.

In addition, in the conventional technology, conductivity and permittivity of the tissue is estimated from Equations 5 and 6 given below, using the water content in the tissue acquired from Equation 3 and Equation 4.

$$\sigma = \sigma_w \frac{W}{1+(1-W)/2} \quad \text{Equation 5}$$

Herein, $\sigma_w$ denotes conductivity of an ionic solution.

$$\varepsilon_r = \varepsilon_w \frac{3\varepsilon_p + 2W(\varepsilon_w - \varepsilon_p)}{4\varepsilon_w - \varepsilon_p + 2W(\varepsilon_p - \varepsilon_w)} \quad \text{Equation 6}$$

Herein, $\varepsilon_w$ denotes permittivity of an ionic solution, and $\varepsilon_p$ denotes permittivity of foreign particles.

In the conventional technology, however, it is difficult to analytically solve Equations 5 and 6 because they are non-linear equations. To solve Equations 5 and 6, permittivity of foreign particles needs to be obtained. However, it is substantially impossible to obtain the permittivity of foreign particles in the tissue because cell structures and protein which operate as foreign substances in the tissue come in different sizes and have different constituents.

Further, in the conventional technology, since conductivity and permittivity are calculated by putting the water content acquired from Equation 3 in Equations 5 and 6, an error of estimation of the water content may directly affect calculation of conductivity and permittivity.

As a conventional technology using water content, European Patent Application Publication No. 851,236 discloses a multi echo imaging technique for estimating the water content. According to this technique, an image at the echo time equal to 0 is acquired through extrapolation based on multiple images according to multiple echo times, and the acquired image is used as an image of water content.

However, the image of water content disclosed in the aforementioned document is very vulnerable to main magnetic field inhomogeneity and radiofrequency field inhomogeneity. Accordingly, it is difficult to clinically utilize the image.

RELATED DOCUMENTS

Patent Document

European Patent Application Publication No. 851,236 (Title of Invention: A method and an automatic system for obtaining water-content and/or electric-permittivity maps from magnetic resonance images)

U.S. Pat. No. 8,064,674 (Title of Invention: Robust classification of fat and water images from 1-point-Dixon reconstructions)

U.S. Pat. No. 6,397,095 (Title of Invention: Magnetic resonance—electrical impedance tomography)

SUMMARY OF THE INVENTION

Therefore, the present invention has been made in view of the above problems, and it is an object of the present invention to provide an apparatus and method for electrical properties tomography using magnetic resonance capable of accurately acquiring the values of conductivity and permittivity, which vary in tissue, with the minimum error by acquiring a water content model and electrical property model of brain tissues based on the spin-lattice relaxation time and water content for a conventionally known tissue portion.

Another object of the present invention is to provide an apparatus and method for electrical properties tomography using magnetic resonance which is capable of obtaining electrical properties images for conductivity and permittivity of brain tissues with high spatial resolution and high accuracy without using a derivative which significantly amplifies noise in an MRI image.

Another object of the present invention is to provide an apparatus and method for electrical properties tomography using magnetic resonance capable of acquiring images less sensitive to noise effects and other damages and thus can be efficiently utilized for clinical diagnosis, by calculating water content in a tissue and acquiring a conductivity image and permittivity image from the calculated water content.

Another object of the present invention is to provide an apparatus and method for electrical properties tomography using magnetic resonance which is capable of attenuating the influence of an error resulting from main magnetic field inhomogeneity or radiofrequency field inhomogeneity by acquiring water content from the ratio between two MRI signals according to two different repetition times.

Another object of the present invention is to provide an apparatus and method for electrical properties tomography using magnetic resonance capable of minimizing errors which may be produced in a calculation operation for acquisition of conductivity and permittivity by providing an electrical property model capable of acquiring the conductivity and permittivity from the ratio between two MRI signals according to two different repetition times.

In accordance with an aspect of the present invention, the above and other objects can be accomplished by the provision of an apparatus for electrical properties tomography using magnetic resonance, the apparatus including a radiofrequency (RF) pulse application unit configured to apply two RF pulses at intervals of different repetition times, an image signal acquisition unit configured to acquire two magnetic resonance imaging (MRI) signals through the applied RF pulses, a water content calculator configured to create a water content model from the correlation between an image ratio and water content for the acquired two MRI signals and to calculate water content of a brain tissue from the created water content model, and an electrical properties image capture unit configured to create an electrical property model from the correlation between water content and electrical properties, calculate the electrical properties from the calculated water content using the created electrical property model, and acquire an electrical properties images to calculate the electrical properties.

The water content calculator may derive a water content modeling function from correlating water content and the image ratio values of brain tissues of cerebrospinal fluid (CSF), white matter and gray matter, and calculate the water content using the derived modeling function.

The electrical properties image capture unit may derive an electrical property modeling function from the correlation between the water content and the electrical properties from water content and spin-lattice relaxation time for brain tissues of cerebrospinal fluid (CSF), white matter and gray matter.

The electrical properties image capture unit may acquire the electrical properties image using the derived electrical property modeling function.

The image signal acquisition unit may acquire the two MRI signals from two spin echo signals generated by the applied RF pulses when an echo time TE passes.

In accordance with another aspect of the present invention, there is provided a method for electrical properties tomography using magnetic resonance, the method including applying two radiofrequency (RF) pulses at intervals of different repetition times, acquiring two magnetic resonance imaging (MRI) signals through the applied RF pulses, creating a water content model from the correlation between an image ratio and water content for the acquired two MRI signals and calculating water content of a brain tissue from the created water content model, and creating an electrical property model from the correlation between water content and electrical properties, calculating the electrical properties from the calculated water content using the created electrical property model, and acquiring an electrical properties images to calculate the electrical properties.

The calculating of the water content may include deriving a water content modeling function from correlating water content and the image ratio values of brain tissues of cerebrospinal fluid (CSF), white matter and gray matter, and calculating the water content using the derived modeling function.

The acquiring of the electrical properties image may include deriving an electrical property modeling function from the correlation between the water content and the electrical properties from water content and spin-lattice relaxation time for brain tissues of cerebrospinal fluid (CSF), white matter and gray matter.

According to an embodiment of the present invention, the values of conductivity and permittivity, which vary in tissue, may be accurately acquired by acquiring a water content model and electrical property model of brain tissues based on the spin-lattice relaxation time and water content for a conventionally known tissue portion.

According to an embodiment of the present invention, electrical properties images for conductivity and permittivity of brain tissues may be obtained with high spatial resolution and high accuracy, without using a derivative which significantly amplifies noise in an MRI image.

According to an embodiment of the present invention, images having less noise and less damages may be obtained and thus be efficiently utilized for clinical diagnosis, by calculating water content in a tissue and acquiring a conductivity image and permittivity image from the calculated water content image.

According to an embodiment of the present invention, the influence of an error resulting from main magnetic field inhomogeneity or radiofrequency field inhomogeneity may be reduced by acquiring water content from the ratio between two MRI signals according to two different repetition times.

According to an embodiment of the present invention, errors which may be produced during a calculation operation for acquisition of conductivity and permittivity, may be minimized by providing an electrical property model capable of acquiring the conductivity and permittivity from the ratio between two MRI signals according to two different repetition times.

BRIEF DESCRIPTION OF THE DRAWINGS

The above and other objects, features and other advantages of the present invention will be more clearly understood from the following detailed description taken in conjunction with the accompanying drawings, in which.

DETAILED DESCRIPTION OF THE PREFERRED EMBODIMENTS

Reference will now be made in detail to the preferred embodiments of the present invention, examples of which are illustrated in the accompanying drawings. However, the present invention is not limited or defined by the illustrated embodiments.

Terms used in this specification are merely adopted to explain specific embodiments, and are not intended to limit the present invention. A singular expression includes a plural expression unless the two expressions are contextually different from each other. In this specification, a term "comprises" and/or "comprising" is intended to indicate that constituents, steps, operations, and/or devices disclosed in this specification does not exclude presence or addition of one or more other constituents, steps, operations, and/or devices.

As used herein, "embodiment", "example", "expect", and "illustration" should not be construed as meaning that an aspect or design is preferred or advantageous over other aspects or designs.

As used herein, the terms "or" refers to "inclusive or" rather than to "exclusive or". That is, unless stated otherwise or contextually clear, the expression "x uses a or b" should be understood as meaning one of natural inclusive permutations.

As used in this specification and claims, the singular forms "a" and "an" are intended to include the plural forms as well, unless the context clearly indicates otherwise.

As used in this specification and claims, terms including ordinal numbers such as first, second, etc. may be used to explain various components, but the constituents are not limited thereto. These terms are used only for the purpose of distinguishing one constituent from another.

Unless defined otherwise, all terms (including scientific and technological terms) used in this specification and appended claims may be construed as having meaning commonly known to those skilled in the art. Terms defined in typical dictionaries should not be interpreted ideally or excessively.

In describing the present invention, a detailed description of well-known functions and constituents will be omitted if it is determined that such description can unnecessarily obscure the main points of the present invention. In addition, terms which will be used below are defined in consideration of the functions of the corresponding elements in the present invention. The definitions of the terms may vary depending on intention of a user, a precedent case, or the like. Therefore, the terms should be defined based on the entire specification.

Figure 1:
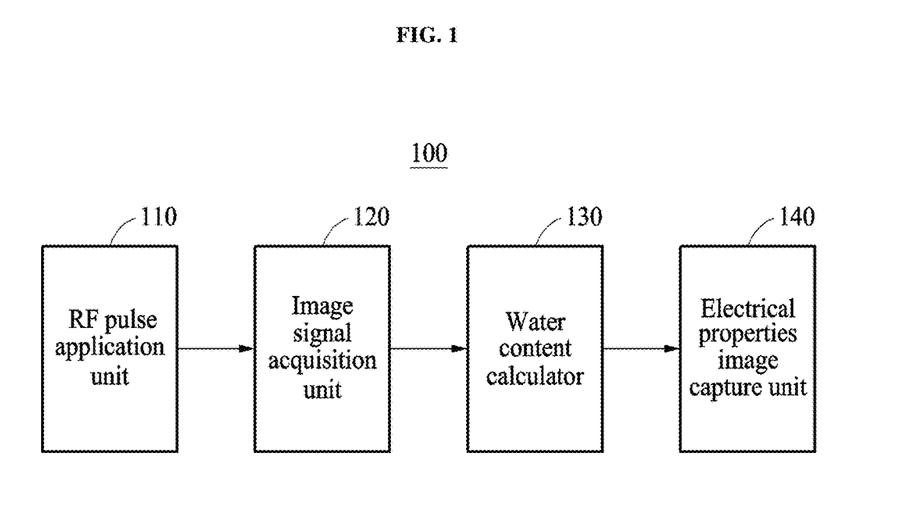
FIG. 1 is a block diagram illustrating configuration of an apparatus for electrical properties tomography using magnetic resonance according to an embodiment of the present invention.

FIG. 1 is a block diagram illustrating configuration of an apparatus for electrical properties tomography using magnetic resonance according to an embodiment of the present invention.

Referring to FIG. 1, an apparatus 100 for electrical properties tomography using magnetic resonance according to an embodiment of the present invention creates a water content model from an image ratio for two MRI signals acquired through a radiofrequency pulse, and calculates water content from the created water content model.

The apparatus 100 for electrical properties tomography creates an electrical property model for correlation between water content and electrical properties, calculates electrical properties from the calculated water content using the electrical property model, and acquires electrical properties images to calculate the electrical properties.

To this end, the apparatus 100 for electrical properties tomography includes a radiofrequency pulse application unit 110, an image signal acquisition unit 120, a water content calculator 130 and an electrical properties image capture unit 140.

The radiofrequency pulse application unit 110 applies two radiofrequency pulses generated at the intervals of different repetition times.

The repetition times, which represent time intervals for generating radiofrequency pulses used to acquire MRI signals, may determine the degree of spin-lattice relaxation.

The radiofrequency pulse application unit 110 may apply a radiofrequency pulse of 90° and then a radiofrequency pulse of 180° at the intervals of different repetition times.

The repetition time represents duration from the time at which a radiofrequency pulse of 90° and a radiofrequency pulse of 180° are applied to the time at which another radiofrequency pulse of 90° is applied. The different repetition times may include a long repetition time (TR1) and a short repetition time (TRs), which are defined by the relative lengths thereof.

The image signal acquisition unit 120 acquires two MRI signals through the applied radiofrequency pulses.

The image signal acquisition unit 120 may acquire two MRI signals from a spin echo signal produced after an echo time passes according to the applied radiofrequency pulses.

The echo time, which represents the time taken to obtain an echo signal after an initial radiofrequency pulse is output, may determine the degree of spin-spin relation.

The spin echo technique may represent a method for capturing a spin echo signal when a radiofrequency pulse of 180° is applied after a radiofrequency pulse of 90° is applied.

The spin echo technique may vary the echo time which represents the time taken to obtain an echo signal from the time at which a radiofrequency pulse of 180° is applied after a radiofrequency pulse of 90° is applied.

Thereby, the image signal acquisition unit 120 may acquire two MRI signals from a spin echo signal according to the spin echo technique, based on the two radiofrequency pulses generated by the radiofrequency pulse application unit 110 at the interval of the two different times.

Hereinafter, a description will be given of two MRI signals of an apparatus for electrical properties tomography using magnetic resonance, with reference to FIGS. 2A and 2B.

Figure 2A:
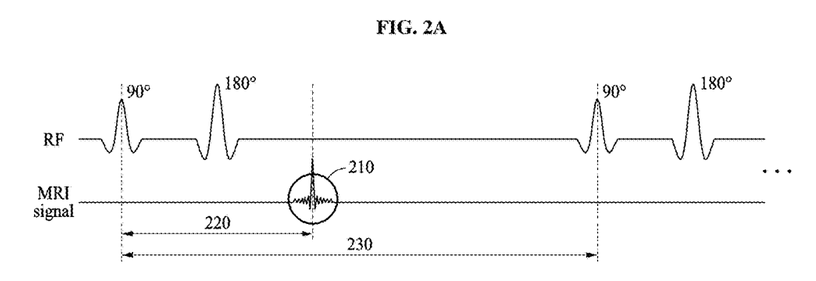
FIGS. 2A and 2B illustrate two MRI signals of an apparatus for electrical properties tomography using magnetic resonance according to an embodiment of the present invention.
Figure 2B:
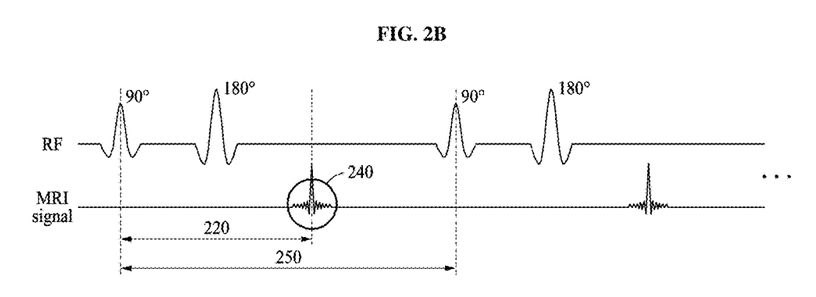

FIGS. 2A and 2B illustrate two MRI signals of an apparatus for electrical properties tomography using magnetic resonance according to an embodiment of the present invention.

FIG. 2A illustrates a long repetition time 230 during which a radiofrequency (RF) pulse of 90° is applied, an RF pulse of 180° is applied, and then another RF pulse of 90° is applied.

Referring to FIG. 2A, an MRI signal generated by RF pulses generated at the intervals of the long repetition time 230 may be verified from a spin echo signal 210 generated when an echo time 220 passes according to the applied RF pulse.

FIG. 2B illustrates a short repetition time 250 during which an RF pulse of 90° is applied, an RF pulse of 180° is applied, and then another RF pulse of 90° is applied.

Referring to FIG. 2B, an MRI signal generated by RF pulses generated at the intervals of the short repetition time 250 may be verified from a spin echo signal 240 generated when the echo time 220 passes according to the applied RF pulse.

The spin echo signals 210 and 240 in FIGS. 2A and 2B may be determined by the spin density at a specific pixel in an MRI image, a spin-lattice relaxation time T1 and a spin-spin relaxation time T2.

Referring back to FIG. 1, the water content calculator 130 creates a water content model for correlation between an image ratio for two acquired MRI signals and water content, and calculates water content of brain tissue from the created water content model.

The image ratio for the MRI signals may be acquired by two MRI signal acquired by the image signal acquisition unit 120 and spin-lattice relaxation time of the brain tissue.

The water content calculator 130 may derive a water content modeling function from the water content and the image ratio of the obtained MRI signals.

The water content modeling function may be derived from a conventionally known correlation between an image ratio and water content for brain tissues of cerebrospinal fluid (CSF), white matter and gray matter.

Hereinafter, a description of the given of a conventionally known correlation between an image ratio and water content for brain tissues of CSF, white matter and gray matter.

Figure 3:
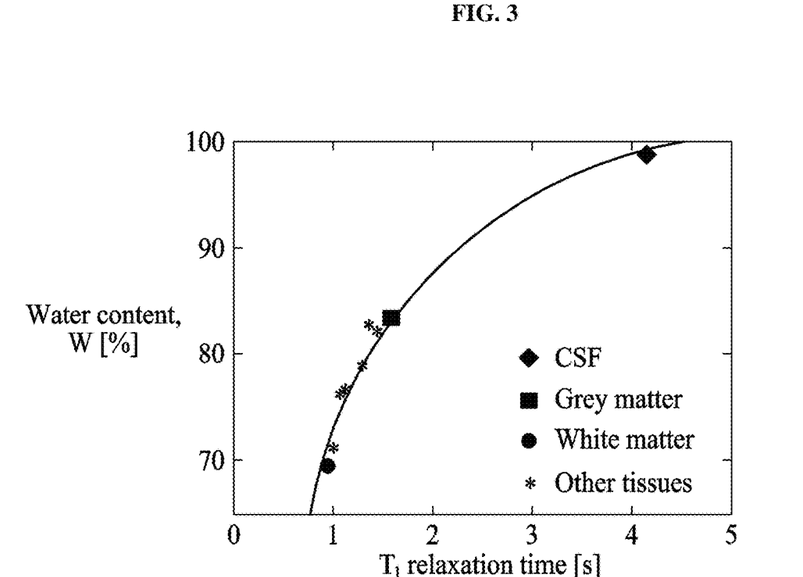
FIG. 3 illustrates a result of modeling of spin-lattice relaxation time with respect to water content of brain tissue.

FIG. 3 illustrates a result of modeling of spin-lattice relaxation time with respect to water content of brain tissue.

More specifically, FIG. 3 is a graph depicting a result of modeling of water content W with respect to spin-lattice relaxation time $T_1$ for the brain tissues of CSF, white matter and gray matter, which occupy the most part of the brain.

It can be seen from FIG. 3 that CSF exhibits water content of about 99% according to a spin-lattice relaxation time of about 4 sec, and the gray matter presents water content of about 83% according to a spin-lattice relaxation time of about 1.5 sec, and the white matter presents water content of about 70% according to a spin-lattice relaxation time of about 1 sec.

As can be seen from FIG. 3, there is a high correlation between the spin-lattice relaxation time and water content not only for the brain tissues of the CSF, gray matter and white matter but also for other tissues.

Referring back to FIG. 1, the water content calculator 130 may calculate water content using a derived modeling function.

Hereinafter, a description will be given for the water content model created through the apparatus 100 for electrical properties tomography using magnetic resonance.

Embodiment

The apparatus 100 for electrical properties tomography using magnetic resonance creates a water content model by correlating an image ratio and water content for two MRI signals, and calculates water content images of brain tissue from the created water content model.

A water content modeling function may be derived from the correlation between the image ratio and water content for the brain tissues of the CSF, white matter and gray matter.

The water content model may be created through the apparatus 100 for electrical properties tomography, using a water content modeling function of Equation 7 below, which is an exponential function.

$$W = w_1 \exp^{-w_2 I_r} \quad \text{Equation 7}$$

Herein, $I_r$ denotes an image ratio for MRI signals, $w_1$ and $w_2$ denote modeling coefficients acquired from an MRI image of a conventionally known brain tissue.

In this embodiment, the modeling factors of Equation 7 may be calculated as $w_1 = 1.525$ and $w_2 = 1.443$ for the brain tissues of the CSF, white matter and gray matter.

Herein, a description will be given of a result of modeling water content using a water content model in an apparatus for electrical properties tomography using magnetic resonance according to an embodiment of the present invention, with reference to FIG. 4.

Figure 4:
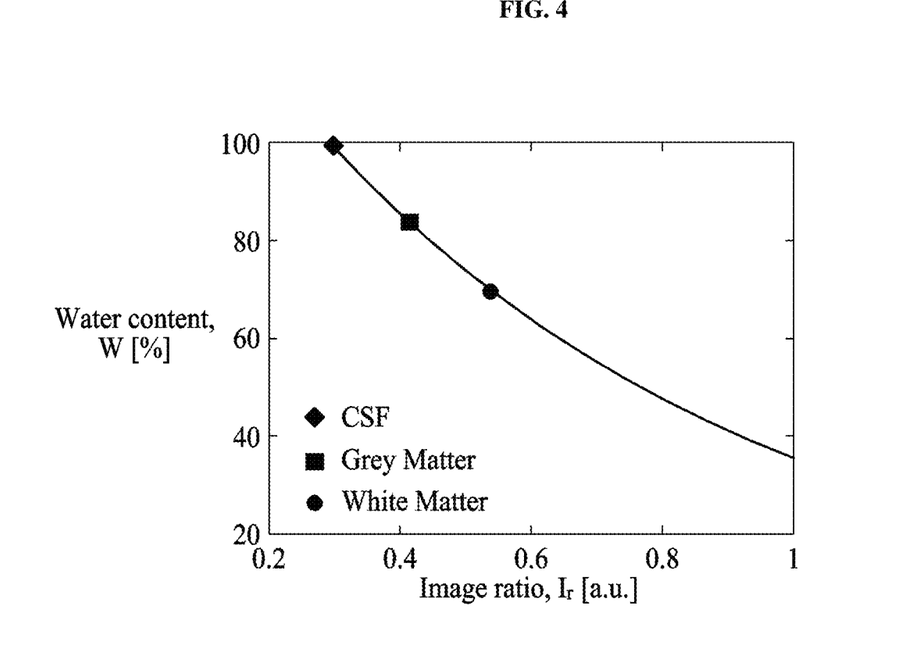
FIG. 4 illustrates a result of modeling of water content with respect to a image ratio of a brain tissue using a water content model according to an embodiment of the present invention.

FIG. 4 illustrates a result of modeling of water content with respect to an image ratio of a brain tissue using a water content model according to an embodiment of the present invention.

More specifically, FIG. 4 is a graph depicting a result of modeling water content W with respect to the image ratio $I_r$ of the brain tissues of the CSF, gray matter and white matter.

Referring to FIG. 4, the CSF presents water content of about 99% according to an image ratio of about 0.3 a.u., the gray matter presents water content of about 83% according to an image ratio of about 0.42 a.u., and the white matter presents water content of about 68% according to an image ratio of about 0.54 a.u.

As can be seen from FIG. 4, the water content model for the apparatus for electrical properties tomography well matches to the actual water content for the brain tissues of the CSF, white matter and gray matter.

Referring back to FIG. 1, the electrical properties image capture unit 140 creates an electrical property model from the correlation between water content and electrical properties, calculates the electrical properties from water content using the created electrical property model, and acquires an electrical properties image to calculate the electrical properties.

The electrical properties image capture unit 140 may derive an electrical property modeling function from the existing correlations between water content and electrical properties and water content and spin-lattice relaxation time for the brain tissues of the CSF, white matter and gray matter.

The electrical properties image capture unit 140 may drive an electrical property modeling function from the electrical property model.

In addition, the electrical properties image capture unit 140 may acquire an electrical properties image using the derived electrical property modeling function.

The electrical properties may include conductivity and permittivity of a human tissue.

Hereinafter, a description will be given of an electrical property model for conductivity and permittivity of the apparatus 100 for electrical properties tomography.

Embodiment

According to an embodiment, the apparatus 100 for electrical properties tomography using magnetic resonance creates an electrical property model for correlation between water content and electrical properties, and calculates conductivity and permittivity of brain tissues from the created electrical property model.

An electrical property modeling function for the correlation between water content and electrical properties may be derived from the water content and spin-lattice relaxation time for the brain tissues of the CSF, white matter and gray matter.

The electrical property model may be created through the apparatus 100 for electrical properties tomography, using the exponential function of Equation 8 and the electrical property modeling function of Equation 9, which is a second order polynomial.

$$\sigma = c_1 + c_2 \exp^{c_3 W} \quad \text{Equation 8}$$

Herein, W denotes water content, and $c_1$, $c_2$ and $c_3$ are the conductivity modeling coefficients acquired from MRI of conventionally known brain tissues.

The conductivity modeling coefficients for MRI of the brain tissues of the CSF, white matter and gray matter may be given as $c_1 = 0.286$, $c_2 = 1.526 \times 10^{-5}$, and $c_3 = 11.852$.

The electrical properties image capture unit 140 may calculate conductivity σ in Equation 8, using water content W satisfying Equation 7.

$$\varepsilon_r = p_1 W^2 + p_2 W + p_3 \quad \text{Equation 9}$$

Herein, W denotes water content, and $p_1$, $p_2$ and $p_3$ are the permittivity modeling coefficients acquired from MRI of conventionally known brain tissues.

The permittivity modeling coefficients for MRI of the brain tissues of the CSF, white matter and gray matter may be given as $p_1 = -287$, $p_2 = 591$, and $p_3 = -220$.

The electrical properties image capture unit 140 may calculate the relative permittivity $\varepsilon_r$ in Equation 9 using water content W satisfying Equation 7.

The electrical properties image capture unit 140 may also quite an electrical properties image for electrical properties including the calculated conductivity and permittivity.

Hereinafter, a description will be given of a result of modeling conductivity and permittivity using an electrical property model in an apparatus for electrical properties tomography using magnetic resonance according to an embodiment of the present invention, with reference to FIGS. 5A and 5B.

Figure 5A:
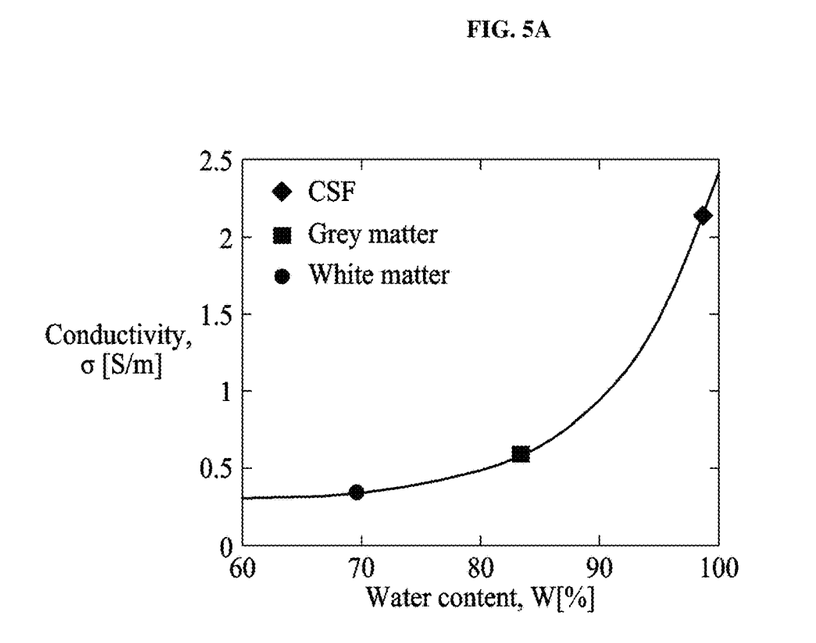
FIGS. 5A and 5B illustrate a result of modeling of conductivity and permittivity with respect to water content of brain tissues using an electrical property model according to an embodiment of the present invention.
Figure 5B:
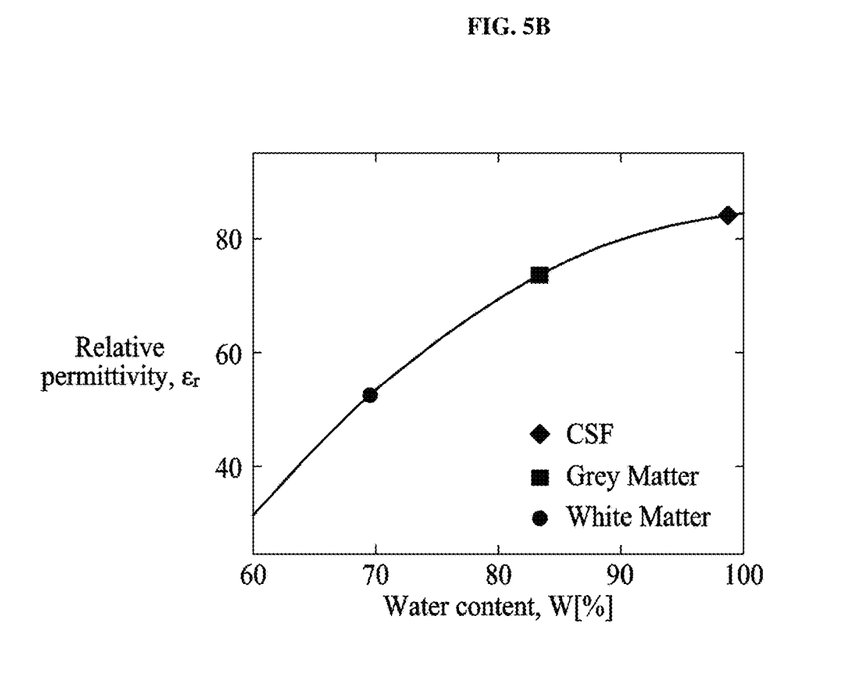

FIGS. 5A and 5B illustrate a result of modeling of conductivity and permittivity with respect to water content of brain tissue using an electrical property model according to an embodiment of the present invention.

More specifically, FIG. 5A is a graph depicting a result of modeling conductivity σ with respect to water content W of the brain tissues of the cerebrospinal fluid CSF, white matter and gray matter, FIG. 5B is a graph depicting a result of modeling permittivity $\varepsilon_r$ with respect to water content W of the brain tissues of the cerebrospinal fluid CSF, white matter and gray matter.

Referring to FIG. 5A, the CSF presents conductivity of about 2.2 S/m according to water content of about 99%, the gray matter presents conductivity of about 0.6 S/m according to water content of about 83%, and the white matter presents conductivity of about 0.3 S/m according to water content of about 70%.

Referring to FIG. 5B, the CSF presents permittivity of about 84 according to water content of about 99%, the gray matter presents permittivity of about 74 according to water content of about 83%, and the white matter presents permittivity of about 53 according to water content of about 70%.

As can be seen from FIGS. 5A and 5B, the electrical property model for the apparatus for electrical properties tomography yields conductivity and permittivity very precisely for the brain tissues of the CSF, white matter and gray matter.

Further, it can be seen that conductivity and permittivity can be accurately estimated for brain tissues other than the CSF, white matter and gray matter through the electrical property model of FIGS. 5A and 5B.

FIGS. 6A to 6D illustrate the electrical properties images, MRI images and water content images of brain tissues acquired using an apparatus for electrical properties tomography using magnetic resonance according to an embodiment of the present invention.

More specifically, FIGS. 6A to 6D shows MRI images, water content images, conductivity images and relative permittivity images of a brain acquired through MRI and displayed 256*256 image pixels with a pixel size of 1 mm*1 mm*5 mm.

Figure 6A:
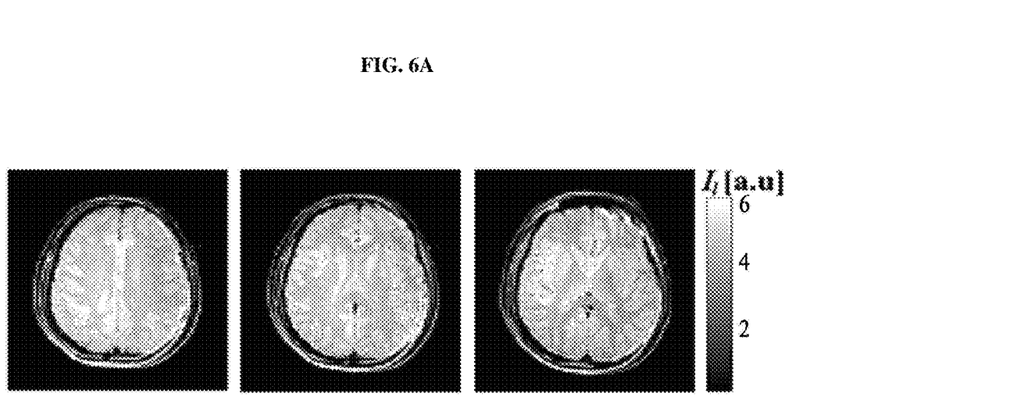
FIGS. 6A to 6D illustrate the electrical properties images, MRI images and water content images of brain tissues acquired using an apparatus for electrical properties tomography using magnetic resonance according to an embodiment of the present invention.
Figure 6B:
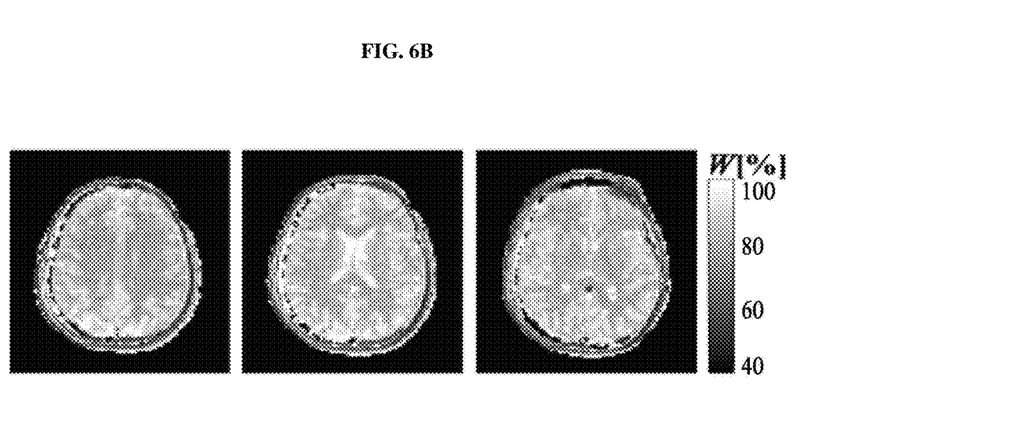

FIG. 6A shows MRI images acquired from RF pulses generated at the intervals of a long repetition time repetition time $TR_1$ of 3000 ms, and FIG. 6B shows images of water content calculated using an image ratio generated from two MRI signals acquired through two RF pulses generated at the intervals of the long repetition time repetition time $TR_1$ of 3000 ms and a short repetition time $TR_s$ of 450 ms, an echo time of 18 ms and a correction constant κ of 0.95.

Figure 6C:
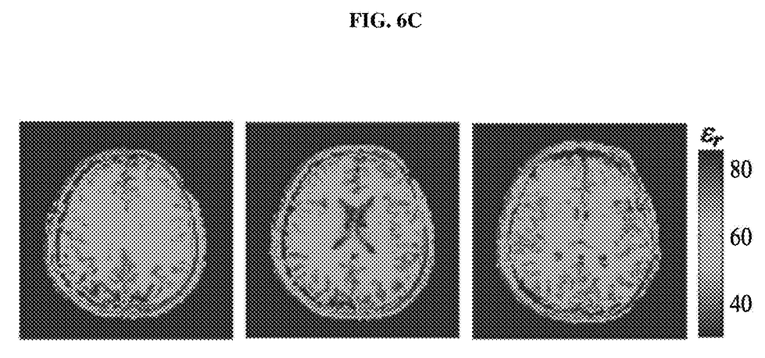
Figure 6D:
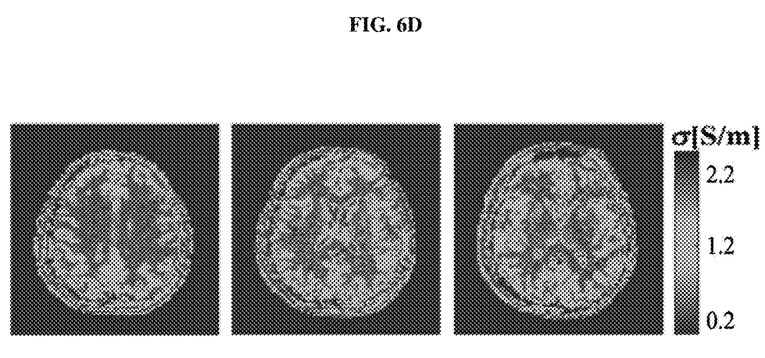

FIG. 6C shows the permittivity images for permittivity calculated from water content, and FIG. 6D shows the conductivity images for conductivity calculated from water content.

As shown in FIGS. 6A to 6D, electrical properties images for conductivity and permittivity of brain tissues may be acquired with a high spatial resolution and high accuracy, using an image ratio and water content for MRI signals acquired using the apparatus for electrical properties tomography of the embodiment.

Figure 7:
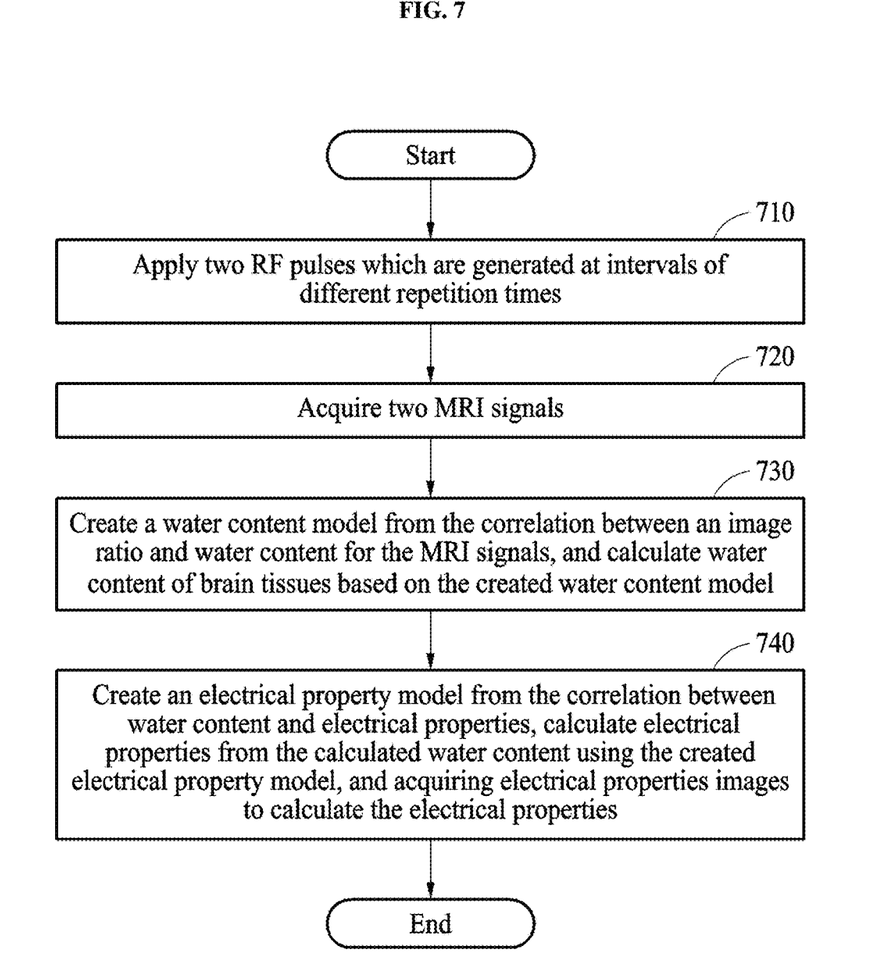
FIG. 7 is a flowchart illustrating a method for electrical properties tomography using magnetic resonance according to an embodiment of the present invention.

FIG. 7 is a flowchart illustrating a method for electrical properties tomography using magnetic resonance according to an embodiment of the present invention.

Referring to FIG. 7, two RF pulses generated at intervals of different repetition times are applied in step 710.

In step 710, an RF pulse of 90° may be applied and then an RF pulse of 180° may be applied at intervals of different repetition times. The repetition times refer to durations from the times of application of an RF pulse of 90° and an RF pulse of 180° to the time of application of another RF pulse of 90°. The different repetition times may include a long repetition time $TR_1$ and a short repetition time $TR_s$, which are different from each other.

In step 720, two MRI signals are acquired.

Step 720 may be a step of acquiring two MRI signals generated when an echo time TE passes according to applied RF pulses.

In step 730, a water content model is created by correlating the image ratio of the MRI signals and the tissue water content. Water content of brain tissues is calculated based on the created water content model.

Step 730 may include deriving a water content modeling function from the correlation of water contents and the image ratio for the known brain tissues of the CSF, white matter and gray matter and calculating water contents using the derived modeling function.

Step 730 may include acquiring a water content image by placing the image ratio into the derived modeling function.

In step 740, an electrical property model for correlation between water content and electrical properties is created, electrical properties are calculated from the calculated water content using the created electrical property model, and electrical properties images are acquired from the calculated electrical property model.

Step 740 may include deriving the electrical property modeling function for correlation between water content and electrical properties from the water content and spin-lattice relaxation time for the CSF, white matter and gray matter.

Step 740 may also include acquiring electrical properties images using the derived electrical property modeling function.

The electrical property modeling function may include a conductivity modeling function for acquiring conductivity images of brain tissues and a permittivity modeling function for acquiring permittivity image of the brain tissue.

The methods described above may be implemented in the form of problem commands executable through various computer means and written in a computer readable medium. The computer readable medium may include program, data files, or a combination thereof. The program commands written in the computer readable medium may be specifically designed or configured for the embodiments or may be well known to those skilled in the art of computer software. Examples of the computer readable recording medium include magnetic media such as a hard disk, a floppy disk and a magnetic tape, optical media such as CD-ROM and DVD, magneto-optical media such as an optical disk, and hardware device such as ROM, RAM and flash memory which are specifically designed to store and execute program commands. Examples of program commands include mechanical language codes created by a compiler and advanced language codes executable on a computer using, for example, an interpreter. The hardware devices may be configured to operate as one or more software modules to perform operations in the embodiments, or vice versa.

Although exemplary embodiments of the present invention have been disclosed for illustrative purposes, those skilled in the art will appreciate that various modifications, additions and substitutions are possible, without departing from the scope and spirit of the invention as disclosed in the accompanying claims. For example, proper result may be achieved even if the techniques described above are implemented in an order different from that for the disclosed method, and/or disclosed constituents such as a system, structure, device and circuit are coupled to or combined with each other in a form different from that for the disclosed method or replaced by other constituents or equivalents.

Therefore, it is intended that the present invention covers the modifications and variations of the present invention provided they come within the scope of the appended claims and their equivalents.

What is claimed is:

1. An apparatus for electrical properties tomography using magnetic resonance, the apparatus comprising:
   a radiofrequency (RF) pulse application unit configured to apply two RF pulses at intervals of different repetition times;
   an image signal acquisition unit configured to acquire two magnetic resonance imaging (MRI) signals through the applied RF pulses;
   a water content calculator configured to create a water content model from the correlation between an image ratio and water content for the acquired two MRI signals and to calculate water content of a brain tissue from the created water content model; and
   an electrical properties image capture unit configured to create an electrical property model from the correlation between water content and electrical properties, calculate the electrical properties from the calculated water content using the created electrical property model, and acquire an electrical properties images to calculate the electrical properties.

2. The apparatus according to claim 1, wherein the water content calculator derives a water content modeling function from correlating water content and the image ratio values of brain tissues of cerebrospinal fluid (CSF), white matter and gray matter, and calculates the water content using the derived modeling function.

3. The apparatus according to claim 1, wherein the electrical properties image capture unit derives an electrical property modeling function from the correlation between the water content and the electrical properties from water content and spin-lattice relaxation time for brain tissues of cerebrospinal fluid (CSF), white matter and gray matter.

4. The apparatus according to claim 3, wherein the electrical properties image capture unit acquires the electrical properties image using the derived electrical property modeling function.

5. The apparatus according to claim 1, wherein the image signal acquisition unit acquires the two MRI signals from two spin echo signals generated by the applied RF pulses when an echo time TE passes.

6. A method for electrical properties tomography using magnetic resonance, the method comprising:
   applying two radiofrequency (RF) pulses at intervals of different repetition times;
   acquiring two magnetic resonance imaging (MRI) signals through the applied RF pulses;
   creating a water content model from the correlation between an image ratio and water content for the acquired two MRI signals and calculating water content of a brain tissue from the created water content model; and
   creating an electrical property model from the correlation between water content and electrical properties, calculating the electrical properties from the calculated water content using the created electrical property model, and acquiring electrical properties images to calculate the electrical properties.

7. The method according to claim 6, wherein the calculating of the water content comprises:
   deriving a water content modeling function from correlating water content and the image ratio values of brain tissues of cerebrospinal fluid (CSF), white matter and gray matter, and calculating the water content using the derived modeling function.

8. The method according to claim 6, wherein the acquiring of the electrical properties image comprises:
   deriving an electrical property modeling function from the correlation between the water content and the electrical properties from water content and spin-lattice relaxation time for brain tissues of cerebrospinal fluid (CSF), white matter and gray matter.

9. A computer readable recording medium for recording a program for executing the method according to any one of claims 6 to 8.

* * * * *